(12) United States Patent
Asano et al.

(10) Patent No.: US 10,570,426 B2
(45) Date of Patent: *Feb. 25, 2020

(54) METHOD FOR PRODUCING METHACRYLIC ACID ESTER AND NOVEL METHACRYLIC ACID ESTER SYNTHETASE

(71) Applicant: Mitsubishi Chemical Corporation, Tokyo (JP)

(72) Inventors: Yasuhisa Asano, Toyama (JP); Eiji Sato, Kanagawa (JP); Fujio Yu, Kanagawa (JP); Wataru Mizunashi, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 232 days.

This patent is subject to a terminal disclaimer.

(21) Appl. No.: 15/124,331

(22) PCT Filed: Mar. 5, 2015

(86) PCT No.: PCT/JP2015/001186
§ 371 (c)(1),
(2) Date: Sep. 7, 2016

(87) PCT Pub. No.: WO2015/133146
PCT Pub. Date: Sep. 11, 2015

(65) Prior Publication Data
US 2017/0022525 A1  Jan. 26, 2017

(30) Foreign Application Priority Data
Mar. 7, 2014 (JP) .................................. 2014-044880

(51) Int. Cl.
*C12P 7/62* (2006.01)
*C12N 9/10* (2006.01)

(52) U.S. Cl.
CPC .................. *C12P 7/62* (2013.01); *C12N 9/10* (2013.01); *C12N 9/1029* (2013.01); *C12Y 203/01* (2013.01)

(58) Field of Classification Search
None
See application file for complete search history.

(56) References Cited

U.S. PATENT DOCUMENTS

| 2009/0130729 | A1 | 5/2009 | Symes et al. | |
| 2010/0035314 | A1 | 2/2010 | Mueller et al. | |
| 2013/0065279 | A1* | 3/2013 | Burk | C12P 19/32 435/88 |
| 2015/0184207 | A1* | 7/2015 | Sato | C12P 7/62 435/135 |
| 2015/0191756 | A1 | 7/2015 | Sato et al. | |

FOREIGN PATENT DOCUMENTS

| CA | 2 688 292 A1 | 12/2008 |
| CN | 104619851 A | 5/2015 |
| CN | 104769123 A | 7/2015 |
| EP | 2 848 694 A1 | 3/2015 |
| EP | 2 894 224 A1 | 7/2015 |
| JP | 5-64589 A | 3/1993 |
| JP | 10-248578 A | 9/1998 |
| JP | 10-337185 A | 12/1998 |
| JP | 2011-200133 A | 10/2011 |
| WO | 00/32789 A1 | 6/2000 |
| WO | WO 2005/090586 A1 | 9/2005 |
| WO | 2007/039415 A1 | 4/2007 |
| WO | 2007/110394 A2 | 10/2007 |
| WO | 2008/145737 A1 | 12/2008 |
| WO | 2009/135074 A2 | 11/2009 |
| WO | 2011/031897 A1 | 3/2011 |
| WO | 2012/135789 A2 | 10/2012 |
| WO | 2014/038214 A1 | 3/2014 |

OTHER PUBLICATIONS

Kalua & Boss, "Evolution of Volatile Compounds during the Development of Cabernet Sauvignon Grapes (*Vitis vinifera* L.)", J. Agric. Food Chem. 2009, 57, 3818-3830. DOI:10.1021/jf803471n.*
Office Action dated Jun. 18, 2018 in Korean Patent Application No. 10-2016-7022513 (with English translation), 7 pages.
Partial Supplementary European Search Report dated Feb. 1, 2017 in Patent Application No. 15759063.9.
Office Action dated Nov. 1, 2016 in Australian Patent Application No. 2015225348.
Office Action dated Aug. 29, 2017 in Japanese Patent Application No. 2015-515322 (with unedited computer generated English translation).
Chiaki Yoshikawa, et al. "Identification of aromatic compounds in plants and characterization of alcohol acyltransferase", Annual Meeting of the Japan Society for Bioscience, Biotechnology, and Agrochemistry, 2014, 3 pages (with full English language translation).
Ying-Xin Zhang, et al., "Genes encoding acyl-CoA dehydrogenase (AcdH) homologues from *Streptomyces coelicolor* and *Streptomyces avermitilis* provide insights into the metabolism of small branched-chain fatty acids and macrolide antibiotic production", Microbiology, vol. 145, pp. 2323-2334, (1999).

(Continued)

*Primary Examiner* — Suzanne M Noakes
(74) *Attorney, Agent, or Firm* — Oblon, McClelland, Maier & Neustadt, L.L.P.

(57) ABSTRACT

Provided is a method for producing a methacrylic acid ester using a biocatalyst, said method comprising a step of reacting an alcohol or a phenol with methacrylyl-CoA in the presence of an alcohol acyltransferase originated from a plant selected from the group consisting of a plant belonging to the genus *Osmanthus*, a plant belonging to the genus *Vitis*, a plant belonging to the genus *Citrus*, a plant belonging to the genus *Durio*, a plant belonging to the genus *Magnolia* and a plant belonging to the genus *Chamaemelum* to thereby synthesize the methacrylic acid ester.

2 Claims, 6 Drawing Sheets

(56) References Cited

OTHER PUBLICATIONS

Birgitta Bremer, et al., "An update of the Angiosperm Phylogeny Group classification for the orders and families of flowering plants: APG III", Botanical Journal of the Linnean Society, vol. 161, pp. 105-121, (2009).
John W. Hawes, et al., "[8] Synthesis of Methacrylyl-CoA and (R)- and (S)-3-Hydroxyisobutyryl-CoA", Methods in Enzymology, vol. 324, Total 4 Pages, (2000).
Sang-Hyun Pyo, et al., "A new route for the synthesis of methacrylic acid from 2-methyl-1,3-propanediol by integrating biotransformation and catalytic dehydration", Green Chem., vol. 14, pp. 1942-1948, (2012).
International Search Report dated Apr. 21, 2015 in PCT/JP15/001186 Filed Mar. 5, 2015.
Office Action dated Aug. 16, 2018 in corresponding European Patent Application No. 15 759 063.9, 6 pages.
Notice of Final Rejection dated Sep. 17, 2018 in Korean Patent Application No. 10-2016-7022513, with English translation.
Office Action dated Sep. 20, 2019, in Indian Patent Application No. 201647030173 (English translation included).
Combined Chinese Office Action and Search Report dated Apr. 16, 2019, in Patent Application No. 201580010994.8 (with partial English translation and English translation of categories of cited documents), 12 pages.

\* cited by examiner

● : protein concentration (mg/ml)、　○ :　AAT activity (mU/ml)

● : 5 0 mM     acetate buffer
■ : 5 0 mM     PIPES buffer
▲ : 5 0 mM     Tris (tris(hydroxymethyl)aminomethane)-HCl buffer
◆ : 5 0 mM     glycine-sodium hydroxide buffer

METHOD FOR PRODUCING METHACRYLIC ACID ESTER AND NOVEL METHACRYLIC ACID ESTER SYNTHETASE

THE NAMES OF THE PARTIES TO A JOINT RESEARCH AGREEMENT

The present invention was made under a Joint Research Agreement between Mitsubishi Rayon Co., Ltd. and Toyama Prefecture. The Joint Research Agreement was in effect on or before the date the present invention was made, and the present invention was made as a result of the activities undertaken within the scope of the Joint Research Agreement.

TECHNICAL FIELD

The present invention relates to a method for producing organic acid esters, especially methacrylic acid esters, using biocatalysts, more specifically, to a method for producing methacrylic acid esters using alcohol acyltransferase capable of producing methacrylic acid esters. Furthermore, the present invention relates to alcohol acyltransferase and a method for using the same.

BACKGROUND ART

Methacrylic acid esters are primarily used as raw material in acrylic resins, while there is great demand for use as comonomers in applications such as paints, adhesives, and resin modifiers. Some known examples in industrial manufacturing methods are ACH (acetone cyanohydrin) methods using acetone and hydrogen cyanide as raw materials, and methods for direct oxidation using isobutylene and tert-butyl alcohol as raw materials. Those chemical production methods depend on fossil raw materials and require a great deal of energy.

In recent years, technologies for producing various chemicals from biomass as a carbon source substituting conventional fossil raw materials have attracted attention from the viewpoints of environmental protection and prevention of global warming. Although methacrylic acid esters are also expected to be produced from biomass raw materials, a specific production example from biomass raw materials using a biocatalyst has not been reported.

For example, methods using microorganisms existing in nature to produce 2-hydroxyisobutyric acid and 3-hydroxyisobutyric acid as precursors of methacrylic acid from a natural source such as sugar have been proposed (refer to Patent Literatures 1 and 2, and Non-Patent Literature 1). However, in those methods, the procedures for dehydrating precursors and forming methacrylic acid still depend on chemical techniques.

In addition, methods for forming methacrylic acid from glucose using recombinant microorganisms that do not exist naturally and are produced by introducing multiple enzyme genes have been proposed; however, those methods are results of combining an already known enzyme reaction and a hypothetical enzyme reaction analogized from such reaction, and thus have not been proven (refer to Patent Literatures 3 to 5) In particular, although Patent Literature 5 shows examples of various biocatalysts (hydrolase, wax ester synthetase, alcohol acetyltransferase) having common ester formation activity, it is unclear whether the exemplified biocatalysts have the synthetic activity for methacrylic acid ester.

Furthermore, Patent Literature 6 discloses a method for producing acrylic acid esters through reaction of hydrolase in the presence of acrylyl-CoA and alcohol. The same document suggests that methacrylic acid esters are also produced by such a method. However, when taking account of diversity and substrate specificity of biocatalysts, it merely suggests production of acrylic acid esters by a certain type of hydrolase, and it is unclear whether the hydrolase is capable of producing methacrylic acid esters having different structures. Furthermore, it is totally unclear whether other types of biocatalysts having different reaction mechanisms are capable of producing methacrylic acid esters. In addition, when esters are synthesized by the hydrolase described in Patent Literature 6, it is assumed that the formed ester will be decomposed by the hydrolysis activity in the first place, and thus such a production method is quite unlikely to be effective.

On the other hand, alcohol acetyltransferase has been known as a fruity flavor synthetase. Patent Literature 7 identifies the same enzyme genes contained in specific fruits and proposes synthetic methods of various esters that are of fruit flavors. However, whether methacrylic acid esters are synthesizable with those enzymes is not reported and has been completely unclear.

As stated above, although some proposals or studies have been made, there are no examples of methacrylic acid esters actually produced through enzymatic reactions, and thus the establishment of an effective production method has been desired.

PRIOR ART DOCUMENT

Patent Literature

Patent Literature 1: WO2007/110394
Patent Literature 2: WO2008/145737
Patent Literature 3: WO2009/135074
Patent Literature 4: WO2011/031897
Patent Literature 5: WO2012/135789
Patent Literature 6: WO2007/039415
Patent Literature 7: WO2000/32789
Patent Literature 8: JP2011-200133A
Patent Literature 9: JPH05-64589A
Patent Literature 10: JPH10-337185A
Patent Literature 11: JPH10-24867A

Non-Patent Literature

Non-Patent Literature 1: Green Chemistry, 2012, 14, 1942-1948
Non-Patent Literature 2: Methods in Enzymology, 2000, 324, 73-79
Non-Patent Literature 3: Botanical Journal of the Linnean Society, 2009, 161, 105-121
Non-Patent Literature 4: Microbiology, 1999, 145, 2323-2334

SUMMARY OF THE INVENTION

Problems to be Solved by the Invention

The objective of the present invention is to provide a method for producing a methacrylic acid ester using a biocatalyst. Also, the objective of the present invention is to provide a novel alcohol acyltransferase having synthetic activity for producing a methacrylic acid ester.

Solutions to the Problems

The inventors of the present invention have found that alcohol acyltransferase derived from a certain plant has synthetic activity for producing a methacrylic acid ester, and they have completed the present invention. Moreover, the inventors have produced a novel alcohol acyltransferase from a suspension prepared by using a plant. Namely, the present invention is as follows.

[1] A method for producing a methacrylic acid ester, comprising a step for synthesizing a methacrylic acid ester by reacting alcohol or phenol with methacrylyl-CoA in the presence of an alcohol acyltransferase derived from a plant selected from a group consisting of plants that belong to *Lamiales, Vitales, Sapindales, Malvales, Magnoliales* and *Asterales*.

[2] A method for producing a methacrylic acid ester, comprising a step for synthesizing a methacrylic acid ester by reacting alcohol or phenol with methacrylyl-CoA in the presence of an alcohol acyltransferase derived from a plant selected from a group consisting of plants that belong to Oleaceae, Vitaceae, Rutaceae, Malvaceae, Magnoliaceae and Asteraceae.

[3] A method for producing a methacrylic acid ester, comprising a step for synthesizing a methacrylic acid ester by reacting alcohol or phenol with methacrylyl-CoA in the presence of an alcohol acyltransferase derived from a plant selected from a group consisting of plants that belong to *Osmanthus, Vitis, Citrus, Durio, Magnolia* and *Chamaemelum*.

[4] The method for producing a methacrylic acid ester according to [1]~[3], in which the plant is selected from a group consisting of *Osmanthus fragrans, Vitis vinifera, Citrus×paradisi, Durio zibethinus, Michelia figo* and *Chamaemelum nobile*.

[5] A method for producing a methacrylic acid ester, comprising a step for synthesizing a methacrylic acid ester by reacting alcohol or phenol with methacrylyl-CoA in the presence of an alcohol acyltransferase having the following (1)~(3) physicochemical properties:
(1) producing a methacrylic acid ester by reacting with methacrylyl-CoA in the presence of alcohol or phenol;
(2) having a higher activity on methacrylyl-CoA than on acetyl-CoA; and
(3) having a Km value of 0.5 mM or lower for methacrylyl-CoA.

[6] An alcohol acyltransferase or its composition, having the following (1)~(5) physicochemical properties:
(1) producing a methacrylic acid ester by reacting with methacrylyl-CoA in the presence of alcohol or phenol;
(2) having a higher activity on methacrylyl-CoA than on acetyl-CoA;
(3) having a higher activity on isobutyryl-CoA than on acetyl-CoA;
(4) having a Km value of 0.5 mM or lower for methacrylyl-CoA; and
(5) having an optimum pH of 8~9 when using methacrylyl-CoA and n-butanol as the substrate.

[7] The alcohol acyltransferase or its composition according to [6], which is derived from a plant that belongs to *Asterales*.

[8] The alcohol acyltransferase or its composition according to [7], which is derived from a plant that belongs to Asteraceae.

[9] The alcohol acyltransferase or its composition according to [8], which is derived from a plant that belongs to *Chamaemelum*.

[10] The alcohol acyltransferase or its composition according to [9], which is derived from a plant that belongs to *Chamaemelum nobile*.

[11] A method for producing an organic acid ester using an alcohol acyltransferase or its composition according to any of [6]~[10].

[12] An alcohol acyltransferase, which is derived from a plant selected from a group consisting of *Lamiales, Vitales, Sapindales, Malvales, Magnoliales* and *Asterales*, and which is capable of producing a methacrylic acid ester by reacting with methacrylyl-CoA in the presence of alcohol or phenol.

[13] The alcohol acyltransferase according to [12], in which the plant belongs to Oleaceae, Vitaceae, Rutacea, Malvaceae, Magnoliaceae or Asteraceae.

[14] The alcohol acyltransferase according to [13], in which the plant belongs to *Osmanthus, Vitis, Citrus, Durio, Magnolia* or *Chamaemelum*.

[15] The alcohol acyltransferase according to [14], in which the plant belongs to *Osmanthus fragrans, Vitis vinifera, Citrus×paradisi, Durio zibethinus, Michelia figo* or *Chamaemelum nobile*

[16] The alcohol acyltransferase according to [15], having the following (1)~(6) physicochemical properties:
(1) producing a methacrylic acid ester by reacting with methacrylyl-CoA in the presence of alcohol or phenol;
(2) having a higher activity on methacrylyl-CoA than on acetyl-CoA;
(3) having a higher activity on isobutyryl-CoA than on acetyl-CoA,
(4) having a higher activity on propionyl-CoA than on acetyl-CoA;
(5) having a Km value of 0.5 mM or lower for methacrylyl-CoA; and
(6) having an optimal pH of 8~9 with a substrate of methacrylyl-CoA and n-butanol.

[17] The alcohol acyltransferase according to [16], which is derived from a plant that belongs to Asteraceae.

[18] The alcohol acyltransferase according to [17], which is derived from a plant that belongs to *Chamaemelum*.

[19] The alcohol acyltransferase according to [18], which is derived from a plant that belongs to *Chamaemelum nobile*.

Effects of the Invention

According to the present invention, methacrylic acid esters are produced by using biocatalysts. When the production method of the present invention is combined with in vivo metabolism, fermentative production of methacrylic acid esters is also achieved. As a result, compared with a conventional chemical production process, energy, resources and load on the environment are remarkably reduced when producing methacrylic acid esters. In addition, using a novel enzyme related to the present invention, organic acid esters such as methacrylic acid esters are produced more efficiently.

MODES FOR CARRYING OUT THE INVENTION

Figure 1:
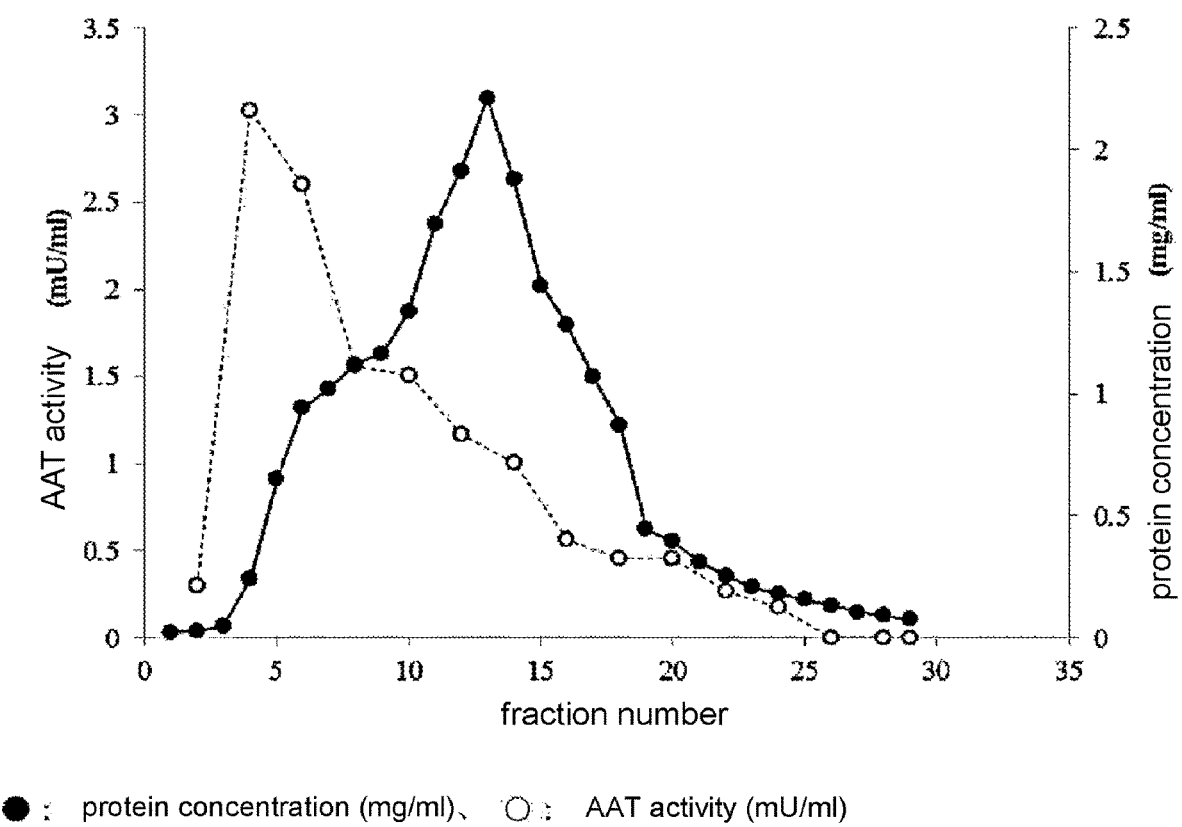
FIG. 1 is a graph showing purification through a DEAE-Toyopearl column (second time) (elution patterns)

In the following, preferred embodiments of the present invention are described with reference to the drawings. However, the embodiments below are shown as examples representing the present invention, and are not intended to limit the scope of the present invention.

1. Method for Producing Methacrylic Acid Ester by Using Alcohol Acyltransferase

[Methacrylic Acid Ester]

In the present invention, a methacrylic acid ester is a compound represented by formula 1 below. In formula 1, "R" indicates a linear- or branched-chain C1~C20 hydrocarbon group. The hydrocarbon group may be saturated or unsaturated acyclic, or saturated or unsaturated cyclic; preferably, a linear- or branched chain unsubstituted C1~C10 alkyl, aralkyl or aryl group. Especially preferred are C1~C8 alkyl, benzyl or phenyl groups such as methyl groups, ethyl groups, n-propyl groups, isopropyl groups, n-butyl groups, isobutyl groups, sec-butyl groups, tert-butyl groups, n-pentyl groups, isopentyl groups, tert-pentyl groups, n-hexyl groups, isohexyl groups, 2-hexyl groups, dimethylbutyl groups, ethylbutyl groups, heptyl groups, octyl groups and 2-ethylhexyl groups.

CH₂=C(CH₃)COO—R                                       (formula 1)

"Methacrylic acid" (IUPAC name: 2-methyl-2-propenoic acid) indicates a compound having the formula below, including any salts or ionized forms thereof. Examples of salts of methacrylic acid are sodium salts, potassium salts, calcium salts, magnesium salts, and the like.

CH₂=C(CH₃)COOH

[Methacrylyl-CoA]

The methacrylyl-CoA related to the present invention is a compound represented by the structural formula below. Methacrylyl-CoA is known as a metabolic intermediate of valine inside organisms. The methacrylyl-CoA used in the present invention may also be produced by a known or novel method. Examples of a known synthetic method are organo-chemically synthesizing a methacrylic anhydride and coenzyme A (Methods in Enzymology, 324, 73-79 (2000)), methods using an enzyme reaction, and the like.

In the present invention, among those, methacrylyl-CoA transformed from isobutyryl-CoA through the action of acyl-CoA dehydrogenase (EC 1.3.99.3) (hereinafter referred to as ACD), or methacrylyl-CoA transformed from 3-hydroxyisobutyryl-CoA through the action of enoyl-CoA hydratase (EC 4.2.1.17) (hereinafter referred to as ECH) is preferred. Furthermore, methacrylyl-CoA used in the embodiments of the present invention may be produced from 2-oxoisovaleric acid by way of isobutyryl-CoA. Namely, using methacrylyl-CoA produced from isobutyryl-CoA or 3-hydroxyisobutyryl-CoA, the method related to the present invention is capable of performing continuous reactions with enzymes, thus achieving an enhancement in yield and a reduction in impurities. Meanwhile, the method is capable of directly producing a methacrylic acid ester without going through a synthetic pathway of methacrylic acid, produced or generated as a byproduct, which is highly toxic to organisms. Using the above method related to the present invention, methacrylic acid esters are produced through in vivo continuous reactions (metabolic fermentation) with a low environmental load.

[Alcohols, Phenols]

The alcohols or phenols, used as raw materials when producing methacrylic acid esters related to the present invention, are compounds represented by formula 2 below. The structure of the alcohol or phenol corresponds to a methacrylic acid ester; therefore, the structure thereof is defined the same as that for "R" in Formula 1, and represents a linear or branched C1-C20 hydrocarbon group. The hydrocarbon group may be saturated or unsaturated acyclic, or saturated or unsaturated cyclic. It is preferably a linear or branched C1-C10 unsubstituted alcohol, aralkyl alcohol or phenol. More preferred are C1-C8 alkyl alcohols, benzyl alcohols or phenols such as methanol, ethanol, n-propanol, isopropanol, n-butanol, isobutanol, sec-butanol, tert-butanol, n-pentylalcohol, isopentyl alcohol, tert-pentyl alcohol, n-hexyl alcohol, isohexyl alcohol, 2-hexyl alcohol, dimethylbutyl alcohol, ethylbutyl alcohol, heptyl alcohol, octyl alcohol, and 2-ethylhexyl alcohols. Especially preferred are methanol, ethanol, n-butanol, isobutanol and n-hexyl alcohol.

R—OH                                                  (formula 2)

[Alcohol Acyltransferase]

The alcohol acyltransferase related to the present invention (hereinafter referred to as AAT) is an enzyme having catalytic activity for synthesizing esters by transferring the acyl group of acyl-CoA to the alcohol or phenol. AAT is considered to contribute to the formation of esters in various fruits. AAT is known to be present in plants such as *Zingiberales* (banana), *Rosales* (strawberry, apple, pear,

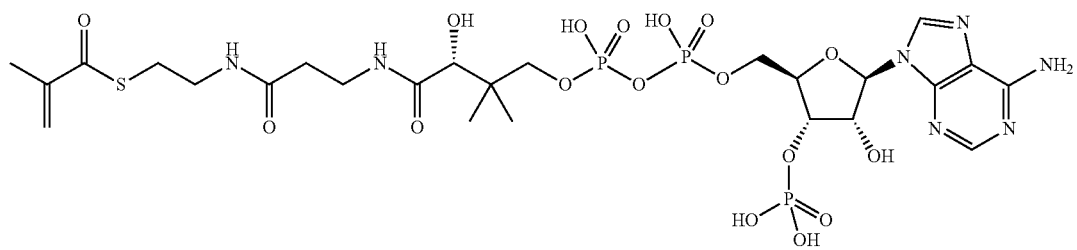

[chem 1]

peach), *Cucurbitales* (melon), *Ericales* (kiwi), *Lamiales* (olive), *Solanales* (tomato), and *Sapindales* (lemon, mango).

The AAT used in the embodiments of the present invention is derived from a plant selected from a group consisting of *Lamiales, Vitales, Sapindales, Malvales, Magnoliales* and *Asterales*. Such an AAT is not limited to any type or origin as long as it is capable of producing a methacrylic acid ester from methacrylyl-CoA and alcohol or phenol as raw materials.

The AAT preferred to be used in the embodiments of the present invention can be easily obtained from the aforementioned plants by employing the following method: obtain an appropriate part of a tissue by cutting the tissue as necessary, add to the cut part a solution containing methacrylyl-CoA and alcohol or phenol represented by the above formula 2, shake the solution, and have it react for a certain duration. By checking the presence of a methacrylic acid ester in the reaction mixture through GC (gas chromatography), the synthetic activity is confirmed. More specifically, leaves, flowers, flower buds, fruit flesh or fruit skins, for example, are cut, to which a solution containing 0.01~10 mM methacrylyl-CoA, and n-butanol at 2~50 molar times the amount of methacrylyl-CoA are added and shaken at 30° C. for 1 to 10 hours. After the reaction was completed, by confirming the presence of a methacrylic acid ester through GC, an AAT applicable to the present invention is achieved.

The enzyme source of AAT preferred to be used in the embodiments of the present invention is a plant selected from a group consisting of *Lamiales, Vitales, Sapindales, Malvales, Magnoliale* and *Asterales*.

Preferred plants belonging to *Lamiales* are Acanthaceae, Bignoniaceae, Byblidaceae, Calceolariaceae, Carlemanniaceae, Gesneriaceae, Lamiaceae, Linderniaceae, Lentibulariaceae, Martyniaceae, Oleaceae, Orobanchaceae, Paulowniaceae, Pedaliaceae, Phrymaceae, Plantaginaceae, Plocospermataceae, Schlegeliaceae, Scrophulariaceae, Stilbaceae, Tetrachondraceae, Thomandersiaceae and Verbenaceae.

Preferred plants belonging to *Vitales* are Vitaceae.

Preferred plants belonging to *Sapindales* are Anacardiaceae, Biebersteiniaceae, Burseraceae, Kirkiaceae, Meliaceae, Nitrariaceae, Rutaceae, Sapindaceae and Simaroubaceae.

Preferred plants belonging to *Malvales* are Bixaceae, Cistaceae, Cytinaceae, Dipterocarpaceae, Malvaceae, Muntingiaceae, Neuradaceae, Sarcolaenaceae, Sphaerosepalaceae and Thymelaeaceae.

Preferred plants belonging to *Magnoliales* are Annonaceae, Degeneriaceae, Eupomatiaceae, Himantandraceae, Magnoliaceae and Myristicaceae.

Preferred plants belonging to *Asterales* are Alseuosmiaceae, Argophyllaceae, Asteraceae, Calyceraceae, Campanulaceae, Goodeniaceae, Menyanthaceae, Pentaphragmataceae, Phellinaceae, Rousseaceae and Stylidiaceae.

Among those listed above, Oleaceae, Vitaceae, Rutaceae, Malvaceae, Magnoliaceae and Asteraceae are more preferred.

In particular, preferred plants belonging to Oleaceae are *Osmanthus, Olea, Jasminum, Forsythia, Syringa, Chionanthus, Fraxinus* and *Ligustrum*; a preferred plant belonging to Verbenaceae is *Glandularia*.

A preferred plant belonging to Lamiaceae is *Salvia*.

Preferred plants belonging to Vitaceae are *Vitis, Ampelopsis, Cayratia, Cissus, Cyphostemma, Leea, Parthenocissus* and *Tetrastigma*.

Preferred plants belonging to Rutaceae are *Citrus, Aegle, Zanthoxylum, Murraya, Ruta, Orixa, Skimmia, Euodia, Phellodendron, Boronia, Acronychia, Clausena, Correa, Glycosmis* and *Melicope*.

Preferred plants belonging to Sapindaceae are *Litchi*.

Preferred plants belonging to Anacardiaceae are *Mangifera*.

Preferred plants belonging to Malvaceae are *Durio, Theobroma, Abutilon, Abelmoschus, Gossypium, Pavonia, Hibiscus, Sida* and *Malva*.

A preferred plant belonging to Magnoliaceae is *Magnolia*, and preferred plants belonging to Asteraceae are *Chamaemelum, Achillea, Echinacea, Matricaria, Tanacetum, Taraxacum, Artemisia, Petasites, Helichrysum, Santolina, Cynara, Silybum, Calendula, Cichorium, Carthamus* and *Chrysanthemum*.

Among those above, especially preferred plants are those belonging to *Osmanthus, Vitis, Citrus, Durio, Magnolia* or *Chamaemelum*.

More specifically, preferred plants belonging to *Osmanthus* are *Osmanthus asiaticus, Osmanthus fragrans, Osmanthus heterophyllus, Osmanthus marginatus, Osmanthus×fortunei* and *Osmanthus insularis*.

A preferred plant belonging to *Olea* is *Olea europaea*.

A preferred plants belonging to *Salvia* is *Salvia splendens*.

A preferred plant belonging to *Glandularia* is *Glandulariaxhybrida*.

Preferred plants belonging to *Vitis* are *Vitis vinifera, Vitis labrusca, Vitis aestivalis, Vitis coignetiae* and *Vitis ficifolia*.

Preferred plants belonging to *Citius* are *Citrus limon, Citrus sudachi, Citrus sphaerocarpa, Citrusxparadisi, Citrus junos, Citrus aurantifolia, Citrus unshiu* and *Citrus sinensis*.

A preferred plant belonging to *Aegle* is *Aegle marmelos*.

A preferred plant belonging to *Litchi* is *Litchi chinensis*.

A preferred plant belonging to *Mangifera* is *Mangifera indica*.

Preferred plants belonging to *Durio* are *Durio zibethinus, Durio testudinarius, Durio kutejensis, Durio oxleyanus, Durio graveolens, Durio dulcis)*.

A preferred plant belonging to *Theobroma* is *Theobroma cacao*.

Preferred plants belonging to *Magnolia* are *Magnolia figo, Magnolia compressa, Magnolia champaca, Magnolia liliiflora, Magnolia kobus, Magnolia obovata* and *Magnolia laevifolia)*.

Preferred plants belonging to *Chamaemelum* are *Chamaemelum nobile* and *Chamaemelum fuscatum*.

Among those listed above, especially preferred are *Osmanthus fragrans, Vitis vinifera, Citrusxparadisi, Durio zibethinus, Magnolia figo* and *Chamaemelum nobile*.

As for the enzyme source in synthetic reactions where a C1~C2 alcohol is the substrate, if a plant is used as is, it is especially preferred to use a plant that belongs to *Vitis* or *Durio* (see Table 1 of later-described examples.)

In the present invention, the classifications of plants are defined based on the APG III system of flowering plant classification (the Botanical Journal of the Linnean Society, 2009, 161, 105121).

In the present invention, upon supplying an AAT for reaction, mode of use is not particularly limited as long as the AAT exhibits the above-mentioned catalytic activity, and the biological tissue containing AAT or processed product thereof can also be used as is. Examples of such biological tissues are an entire plant body, plant organs (such as fruit, leaf, flower petal, stem and seed) and plant tissues (such as fruit skin and fruit flesh). Examples of processed products are a crude AAT enzyme liquid extracted from such biological tissues, purified enzyme thereof, and the like.

To purify AAT is not limited to any specific method, but a preferred isolation method is as follows. After a tissue of an above-listed plant having AAT activity is homogenized, it is suspended in a buffer solution such as a Tris-HCl buffer or phosphate buffer. The obtained crude enzyme liquid is then subjected to a process usually employed for enzyme purification, for example, (1) fractional precipitation, (2) various types of chromatography, (3) dialysis, ultrafiltration, and the like. Those may be used alone or in combination thereof.

A specifically preferable purification process of AAT is as follows. After a biological tissue is frozen by liquid nitrogen or the like and homogenized, AAT is extracted in a five-fold amount of a Tris-HCl buffer containing DTT (dithiothreitol) and glycerol and the like. Next, ion-exchange chromatography is conducted on the crude enzyme extract so as to collect the non-adsorbed portion. Accordingly, an enzyme extract is obtained. As a result of studying methods for preparing a crude enzyme extract, the above method is found to be capable of removing the negative effect of polyphenol contained in a plant so as to efficiently provide a consistent quality of extracts. Furthermore, fractional precipitation with ammonium sulfate or the like is also known to induce enzyme inactivity.

By using ion-exchange chromatograph or gel-filtration column separation or the like on the obtained enzyme extract, the enzyme protein is efficiently purified.

The genetic information of the purified AAT protein is obtained through genetic engineering techniques. The genetic information, isolated or entirely synthesized through a known method, is introduced into a common host-vector system. Using a microorganism transformed by the vector system, the target protein is expressed and is used to produce a methacrylic acid ester related to the present invention.

[Enzymatic Properties of AAT Preferable for Producing Methacrylic Acid Ester]

The AAT related to the present invention reacts with methacrylyl-CoA in the presence of alcohol or phenol so as to catalyze a reaction for producing methacrylic acid ester. It is preferred to use an AAT capable of exhibiting high reactivity when methacrylyl-CoA is the substrate. In particular, it is preferred to use an AAT having higher activity on methacrylyl-CoA than on acetyl-CoA, and having a Km value for the methacrylyl-CoA of 0.5 mM or lower. Using AAT with the above properties, a methacrylic acid ester is produced with high selectivity.

(1) Substrate Specificity

In the present invention, it is preferred to use an AAT having a reactivity that is lower on acetyl-CoA than on methacrylyl-CoA. More specifically, regarding the AAT related to the present invention, when its reactivity on methacrylyl-CoA with n-butanol as the substrate is set as 100%, the reactivity on acetyl-CoA is preferred to be the same or lower, more preferably 50% or lower, even more preferably 40% or lower. Also, when the reactivity on methacrylyl-CoA with n-hexanol as the substrate is set as 100%, the reactivity of the AAT on acetyl-CoA is preferred to be the same or lower, more preferably 70% or lower, even more preferably 50% or lower.

(2) Affinity for Methacrylyl-CoA

The AAT related to the present invention is preferred to exhibit high affinity for methacrylyl-CoA. The affinity for a substrate is evaluated by Michaelis constant (Km). The Km value for methacrylyl-CoA is obtained by measuring/calculating as described in later examples.

The preferred Km value of AAT for methacrylyl-CoA related to the present invention is the same as or lower than the Km value for acetyl-CoA, preferably 0.5 mM or lower, more preferably 0.2 mM or lower, even more preferably 0.1 mM or lower, especially preferably 0.05 mM or lower. When the AAT exhibits a higher affinity level, the aforementioned catalytic reactions are facilitated even with a low concentration of the methacrylyl-CoA as raw material. Accordingly, methacrylic acid esters are produced even more efficiently.

[Recombinant Microorganism for Expression of AAT Activity]

Moreover, for supplying AAT to reactions, the gene of the AAT is isolated and introduced to a conventional host-vector system, which is then used to transform a microorganism. Bacterium hosts are, for example, *E. coli, Rhodococcus, Pseudomonas, Corynebacterium, Bacillus, Streptococcus, Streptomyces* and the like; yeast hosts are *Caccharomyces, Candida, Shizosaccharomyces, Pichia*, and the like; and filamentous fungus hosts are *Aspergillus* and the like. Among them, using *E. coli* is the simplest and most efficient.

The AAT genes of some plants have already been published. Based on such information, DNA probes are prepared, and primers for PCR are formed so that PCR is conducted to isolate the gene. In addition, the base sequence of the AAT gene may also be entirely synthesized by a conventional method. The aforementioned method may be used to check whether or not an AAT with known gene information has synthetic activity for producing a methacrylic acid ester. On the other hand, regarding an AAT with unknown gene information, the AAT is purified and its gene information is obtained by using genetic engineering techniques based on the protein.

In the present invention, preferred AAT genes are not limited specifically as long as the AAT is derived from a plant selected from a group consisting of *Lamiales, Vitales, Sapindales, Malvales, Magnoliales* and *Asterales*, and its translated product is capable of producing a methacrylic acid ester. The AAT gene is appropriately selected from the above-listed AAT enzyme sources.

In the embodiment of the present invention, the AAT gene contains an amino-acid sequence in which one or several amino acids are substituted with, deleted from or added to amino acids in a wild-type amino-acid sequence. The AAT gene also contains the gene encoding the protein that has activity for producing a methacrylic acid ester from methacrylyl-CoA and alcohol.

Here, "several" means 1~40, preferably 1~20, more preferably 10 or fewer. Mutation may be introduced in a gene by a known method such as a Kunkel method or a gapped duplex method, and using a site-directed mutagenesis kit, for example, QuikChange™ Site-Directed Mutagenesis Kit (Stratagene), GeneTailor™ Site-Directed Mutagenesis System (Invitrogen), TaKaRa Site-Directed Mutagenesis System (Mutan-K, Mutan-Super Express Km: Takara Bio). Alternatively, the entire gene having a sequence that includes mutation may be artificially synthesized.

In the embodiments of the present invention, the base sequence of DNA is confirmed by sequence determination by a conventional method. For example, based on Sanger's method, the sequence may be confirmed using an appropriate DNA sequencer.

Moreover, the AAT gene of the present invention contains a gene which encodes a protein identical at least 90%, preferably at least 95%, more preferably at least 99.5%, even more preferably at least 99.9%, to the protein having a wild-type amino-acid sequence, and which has activity for producing a methacrylic acid ester from methacrylyl-CoA and alcohol.

Furthermore, also included in the AAT gene of the present invention are genes which are capable of hybridizing under stringent conditions with a polynucleotide having a base sequence complementary to the wild-type base sequence, and which encode protein having activity for producing a methacrylic acid ester from methacrylyl-CoA and alcohol. Regarding the stringent conditions, an example is as follows: hybridization is performed by maintaining a nylon membrane with fixed DNA at a temperature of 65° C. for 20 hours together with probes in a solution containing 6×SSC (1×SSC is prepared by dissolving 8.76 grams of sodium chloride and 4.41 grams of sodium citrate in 1 liter of water), 1% SDS, 100 μg/mL salmon sperm DNA, 0.1% bovine serum albumin, 0.1% polyvinylpyrrolidone and 0.1% ficoll. But that is not the only option. A person skilled in the art should be able to set conditions for hybridization by taking into account other terms such as probe concentration, length of probe and reaction time in addition to such conditions as salt concentration, temperature of buffer and so forth. Washing conditions after hybridization are, for example, "2×SSC, 0.1% SDS, 42° C." and "1×SSC, 0.1% SDS, 37° C.," and as more stringent conditions, for example, conditions such as "1×SSC, 0.1% SDS, 65° C." and "0.5×SSC, 0.1% SDS, 50° C." may be used.

For a detailed sequence of the hybridization method, refer to Molecular Cloning, A Laboratory Manual 2nd ed. (Cold Spring Harbor Laboratory Press (1989)), Current Protocols in Molecular Biology (John Wiley & Sons (1987-1997)), or the like.

Furthermore, the AAT gene related to the present invention is made up of genes at least 80%, more preferably at least 90%, most preferably at least 95%, identical to those of a wild-type base sequence when calculated using BLAST or the like (for example, default, that is, an initial setting parameter), and contains genes encoding a protein having activity for producing a methacrylic acid ester from methacrylyl-CoA and alcohol. In addition, the codons of the above-mentioned AAT genes may be those modified according to the codon frequency of use in the microorganism host used in genetic transformation.

Here, "sequence identity" is defined by a percentage obtained when two sets of base sequences to be compared are aligned so that their bases match as many as possible, and when the number of matched bases is divided by the total number of bases. For the above-mentioned alignment, an appropriate gap may be inserted into one or both of the two sets of sequences to be compared, if applicable. Such an alignment of sequences can be performed using a known program such as BLAST, FASTA, or CLUSTALW, for example. When a gap is inserted, the above-mentioned total number of bases counts the gap as one. When the total number of bases counted as above is different between the two sequences, the sequence identity (%) is calculated by dividing the matching number of bases by the total number of bases in the longer sequence. The same applies to the identity of amino acid sequences.

In methacrylic acid ester synthetic reactions, a broth obtained by culturing the above-mentioned recombinant microorganisms may be used as is, or bacterial cells collected through centrifugation of the broth or processed products thereof may also be used. Examples of bacterial cell processed products are bacterial cells treated with acetone, toluene or the like, freeze-dried bacterial cells, bacterial homogenates, cell-free extract from the bacterial homogenates, crude enzymes or purified enzymes extracted from those cells or products and so on.

It is an option to synthesize a methacrylic acid ester from a precursor such as isobutyryl-CoA, 3-hydroxyisobutyryl-CoA, 2-oxoisovaleric acid or the like by introducing the ACD gene, ECH gene, BCKAD gene (2-oxoisovalerate dehydrogenase) or the like into a microorganism with the introduced AAT gene, if applicable.

"Precursor" indicates a compound that is inducible into methacrylyl-CoA, that is, isobutyryl-CoA or 3-hydroxyisobutyryl-CoA, and a substance that is inducible into those two compounds.

Examples of a substance inducible to the above two compounds are acids such as 2-oxoisovaleric acid, isobutyric acid, 3-hydroxyisobutyric acid, acetic acid, pyruvic acid, lactic acid, acetoacetic acid, butyric acid, propionic acid, malic acid, fumaric acid, citric acid and succinic acid; amino acids such as valine, alanine, leucine, lysine and glutamic acid, saccharides such as glucose, fructose and xylose, and so on.

To produce methacrylic acid esters from those precursors, it is an option to use various metabolic systems originally contained in a host microorganism, or it is another option for the gene to be introduced into or deleted from the host microorganism, if applicable.

2. Process for Synthesizing Methacrylic Acid Ester

Methacrylic acid esters are produced by the following method: prepare a solution or suspension by adding methacrylyl-CoA and alcohol or phenol represented by the above formula 2 a solvent; then, bring AAT into contact with the solution or suspension so as to react methacrylyl-CoA with the alcohol or phenol while conditions such as temperature and the like are controlled. According to such reactions, a methacrylic group of the methacrylyl-CoA is transferred to the alcohol or phenol of the above formula 2, and a methacrylic acid ester is produced accordingly.

A solution containing the methacrylyl-CoA and alcohol or phenol represented by the above formula 2 is usually prepared using an aqueous medium such as a buffer solution. Here, in order to facilitate the reaction smoothly, the osmolarity and/or ion strength may be controlled by an osmotic pressure regulator or the like. Any type of osmotic pressure regulator may be added as long as it is a water-soluble substance capable of setting the osmotic pressure of the aqueous medium to be isotonic or hypertonic to that of the liquid inside cells. It may be a salt or saccharide, preferably a salt. The salt is preferably a metal salt, more preferably an alkali metal salt, even more preferably an alkali metal halide; for example, sodium chloride and potassium chloride may be used. The saccharide is preferably a monosaccharide or oligosaccharide, more preferably a monosaccharide or disaccharide; for example, glucose, sucrose, mannitol or the like may be used. The osmotic pressure regulator is preferably added at a concentration of at least 1 mM. It is especially preferable to adjust the solution to be isotonic or hypertonic relative to the osmotic pressure of the liquid inside the cell of a living organism to be used.

In addition, to isolate the obtained methacrylic acid ester, it is also an option to add an organic solvent in advance so as to perform reactions in a two-phase system. As for the organic solvent, for example, a linear, branched or cyclic saturated or unsaturated aliphatic hydrocarbon, saturated or unsaturated aromatic hydrocarbon or the like may be used alone or in combination thereof. More specific examples are hydrocarbon solvents (such as pentane, hexane, cyclohexane, benzene, toluene and xylene), halogenated hydrocarbon solvents (such as methylene chloride and chloroform), ether solvents (such as diethyl ether, dipropyl ether, diisopropyl ether, dibutyl ether, tert-butylmethyl ether and dimethoxyethane), ester solvents (such as methyl formate, methyl acetate, ethyl acetate, butyl acetate and methyl propionate), and so forth. When those organic solvents are added, the produced methacrylic acid ester migrates to the organic phase, and the reaction may progress efficiently.

The molar ratios and concentrations of methacrylyl-CoA and alcohol or phenol represented by the above formula 2 in the reaction solution are not limited particularly, and may be set at any rate. In addition, the amount of AAT and reaction conditions are determined appropriately based on the raw materials. Usually, the concentration of each raw material is set to be 0.0000001 to 10 mass % of methacrylyl-CoA, and alcohol or phenol is added at a concentration of 0.1 to 1000 molar times, preferably 0.5 to 500 molar times, the amount of methacrylyl-CoA.

Various other conditions such as the reaction temperature and reaction time are not specifically limited and may be determined appropriately based on the raw materials, enzyme activity, and so on; usually, it is sufficient if reaction is carried out at 5~80° C. for 1 hour to 1 week, preferably, at 10~70° C. for 1 to 120 hours, more preferably at least 1 hour, even more preferably at least 3 hours. The pH of the reaction solution is not particularly limited as long as the reaction progresses efficiently; however, the pH value is preferred to be 4~10, more preferably 5.0~9.0. Conditions such as temperature, time, and the pH of the reaction solution are preferred to be appropriately selected so that the reaction will be completed.

Preferably, under conditions of pH of 5.5~9.0, the concentration of methacrylyl-CoA is adjusted to be directly or indirectly at 0.000001-1 mass %, and the concentration of alcohol or phenol is adjusted to be 1~500 molar times the amount of methacrylyl-CoA. Then, the reaction is carried out for at least one hour at a temperature set at 20~40° C. The raw material (substrate) may be supplied continuously until reaching the above ranges. By so doing, the accumulated concentration of the product is enhanced.

It is also effective to carry out the present reaction under reduced pressure or aeration conditions. That is because the produced methacrylic acid ester is continuously isolated under such conditions, and reactions thereby progress efficiently.

When methacrylic acid esters are produced using methacrylyl-CoA converted through the action of ACD from isobutyryl-CoA as raw material or methacrylyl-CoA converted through the action of ECH from 3-hydroxyisobutyryl-CoA, the reaction is preferred to be carried out under conditions adjusted to be in the above ranges. Here, reactions for synthesizing methacrylyl-CoA using ACD or ECH can be carried out by a known method (for example, as reaction conditions for ACD, the conditions described in Microbiology (1999), 145, pp. 2323-2334). Moreover, in combination with other biological reactions, methacrylic acid esters are produced through continuous reactions (fermentative production) in an organism.

3. Harvesting Methacrylic Acid Ester

The methacrylic acid ester formed in the culture medium or reaction solution and its amount are detected and measured by a conventional method such as high-speed liquid chromatography and LC-MS. In addition, the methacrylic acid ester volatilized in the gas phase (headspace) of the culture container or reaction container and its amount are detected and measured by a conventional method such as gas chromatography.

The methacrylic acid ester is separated from the reaction solution by known methods such as filtration, centrifugation, vacuum concentration, ion exchange or adsorption chromatography, solvent extraction, distillation and crystallization. Those methods may be conducted alone or in combination thereof. The obtained methacrylic acid ester may be polymerized by a known method and used in conventional applications.

Methacrylic acid esters obtained as above and their polymers significantly reduce energy, resources and environmental loads compared with those chemically produced from petroleum, and thus have markedly great social valuables as environmentally low load materials.

4. Novel AAT and Producing Organic Acid Ester Using the Same

A novel AAT as an aspect of the present invention and a production method using such a novel AAT are described below in detail.

The AAT related to the present invention is an enzyme that catalyzes reactions for producing an organic acid ester by the action of acyl-CoA in the presence of alcohol or phenol.

The enzyme composition related to the present invention is not limited to any particular type as long as it contains AAT having synthetic activity for producing a methacrylic acid ester. Examples are biological tissues containing AAT or their treated products, and crude enzyme liquids of AAT extracted from biological tissues or purified enzymes thereof. Examples also include liquid obtained by culturing the aforementioned genetically transformed organisms, bacterial cells harvested from the culture liquids and their treated products, and crude or purified enzymes extracted from the cells or treated products.

(1) Substrate Specificity

The AAT related to the present invention has high reactivity on substrates such as methacrylyl-CoA, propionyl-CoA and isobutyryl-CoA. Namely, the AAT has a higher activity on methacrylyl-CoA, propionyl-CoA and isobutyryl-CoA than on acetyl-CoA. More specifically, when the reactivity of the AAT related to the present invention on methacrylyl-CoA in a substrate of n-butanol is set at 100%, the levels of reactivity on propionyl-CoA and isobutyryl-CoA are approximately the same, whereas the reactivity on acetyl-CoA is about the same or lower, more preferably 50% or lower, even more preferably 40% or lower. Moreover, relative to those three substrates (methacrylyl-CoA, propionyl-CoA and isobutyryl-CoA), the reactivity of AAT on butyryl-CoA and hexanoyl-CoA is 50% or lower, that is, as low as on acetyl-CoA.

(2) Affinity for Methacrylyl-CoA

The AAT related to the present invention has a high affinity for methacrylyl-CoA The affinity for a substrate is evaluated by the Michaelis constant (Km). The Km value for methacrylyl-CoA is measured and calculated according to later-described examples.

Regarding the AAT related to the present invention, its Km value for methacrylyl-CoA is the same as or lower than that for acetyl-CoA, preferably 0.5 mM or lower, more preferably 0.2 mM or lower, even more preferably 0.1 mM or lower, especially preferably 0.05 mM or lower. With a higher affinity level, even when the concentration of methacrylyl-CoA as raw material is low, the aforementioned catalytic reactions will progress, and methacrylic acid esters are thereby produced even more efficiently.

(3) Optimal Reaction pH

The reactivity at a pH of the AAT related to the present invention is recognized in a relatively wide range, such as pH 6~10.5. The optimum pH levels for reactions are 7~9, more particularly, approximately 8~9. Especially, the AAT exhibits the highest activity when a Tris (tris(hydroxymethyl)aminomethane)-HCl buffer at pH 8.5 is used.

(4) Origin

The AAT related to the present invention can be isolated from a plant selected from a group consisting of plants belonging to the aforementioned *Laminales, Vitales, Sapindales, Malvales, Magnoliales* and *Asterales*. The AAT is preferred to be derived from a plant that belongs to Asteraceae, more specifically a plant that belongs to *Chamaemelum*, especially preferably a plant that belongs to *Chamaemelum nobile*.

As described so far, the AAT related to the present invention exhibits excellent characteristics and is significantly useful as an enzyme for synthesizing saturated or unsaturated C3~C4 organic acid esters. Namely, even if unwanted acetyl-CoA is mixed in raw material, the AAT related to the present invention is capable of selectively producing desired organic acid esters. Accordingly, the enzyme related to the present invention exhibits excellent effects in applications where unwanted substances may be mixed in (fermentation production of esters from biomass materials or the like).

EXAMPLES

In the following, the present invention is described in detail by referring to the examples below. However, the scope of the present invention is not limited to the scope of those examples Example 1

Synthesizing Butyl Methacrylate by *Osmanthus fragrans*

Into a vial with a 20 mL-capacity (23×75 mm, made by National Scientific) for headspace GC, 1 gram of chopped leaves of *Osmanthus fragrans* was measured and added. In the vial, 1 mL of a substrate solution (50 mM Tris-HCl (pH 8.5), 40 mM n-butanol, 0.125 mM methacrylyl-CoA) was added. Then, the vial was sealed, and the mixture was reacted at 30° C. for 12 hours. After the completion of reaction, 10 μL of 10 mM 2-hexanon was added as an internal standard, and the produced substance was analyzed by GC-MS using an SPME method (solid-phase microextraction). For SPME, Carboxen/PDMS (75 μm, fused silica, made by Sigma-Aldrich) was used, and the substance was adsorbed at 30° C. for 10 minutes.

Conditions for GC-MS Analysis
  column: TC-70 (inner dia. 0.25 mm×60 m, 0.25 μm, GL Sciences)
  column temperature: 50° C.·5 min→7.5° C./min→200° C.·10 min
  carrier gas: helium
  flow rate: 1.13 mL/min
  injection: 250° C.

In addition, using a 0.1 mM butyl methacrylate solution (50 mM Tris-HCl, pH 8.5), hydrolysis reaction of a methacrylic acid ester by using a leaf of *Osmanthus fragrans* was confirmed. The reaction was carried out at 30° C. for 12 hours.

The amount of produced methacrylic acid ester was calculated by a calibration curve prepared by an internal standard method. A standard solution at each concentration level was prepared in the same volume and container, to which 10 μL of 10 mM 2-hexanon was added as an internal standard, and the reaction mixture was analyzed by SPME and GC-MS methods (n=3). The produced substance was confirmed by comparing its retention time and mass spectrum with those of the standard. In addition, a blank (no substrate) was analyzed at the same time and no production of butyl methacrylate was confirmed. The result is shown in Table 1. A production of 0.7 μM butyl methacrylate by the action of *Osmanthus fragrans* was confirmed.

TABLE 1

| Example | Plant | Product | Concentration (μM) |
|---|---|---|---|
| 1 | *Osmanthus fragrans* (leaf) | butyl methacrylate | 0.7 |
| 2 | *Vitis vinifera* (fruit) | methyl methacrylate | 0.8 |
| 3 | *Vitis vinifera* (fruit) | butyl methacrylate | 9.0 |
| 4 | *Citrus x paradisi* (fruit) | hexyl methacrylate | 0.3 |
| 5 | *Durio zibethinus* (fruit) | ethyl methacrylate | 6.7 |
| 6 | *Durio zibethinus* (fruit) | butyl methacrylate | 14 |
| 7 | *Magnolia figo* (leaf) | butyl methacrylate | 4.4 |
| 7 | *Magnolia figo* (fruit bud) | butyl methacrylate | 0.4 |
| 8 | *Chamaemelum nobile* (leaf) | butyl methacrylate | 6.7 |

Table 2 shows the decomposition activity on butyl methacrylate by the leaf of *Osmanthus fragrans*. A significant reduction in butyl methacrylate was confirmed. The rate of producing a methacrylic acid ester by the action of AAT derived from *Osmanthus fragrans* was indicated to be greater than the rate of decomposing the methacrylic acid ester by the estrase or the like contained in the same plant tissue.

TABLE 2

| Example | Plant | Supplied ester | Remaining rate (%) |
|---|---|---|---|
| 1 | *Osmanthus fragrans* (leaf) | butyl methacrylate | 1.8 |
| 2 | *Vitis vinifera* (fruit) | methyl methacrylate | <1 |
| 3 | *Vitis vinifera* (fruit) | butyl methacrylate | 29 |
| 5 | *Durio zibethinus* (fruit) | ethyl methacrylate | 7.8 |
| 6 | *Durio zibethinus* (fruit) | butyl methacrylate | 9.4 |
| 7 | *Magnolia figo* (leaf) | butyl methacrylate | <1 |
| 7 | *Magnolia figo* (flower bud) | butyl methacrylate | <1 |
| 8 | *Chamaemelum nobile* (leaf) | butyl methacrylate | <1 |

Example 2

Synthesizing Methyl Methacrylate by *Vitis vinifera*

One gram of a finely cut fruit of grape with skin (red glove: *Vitis vinifera*) was measured in a vial, to which 0.5 mL of a substrate solution (50 mM Tris-HCl (pH 8.5), 40 mM methanol, 10 mM methacrylyl-CoA) was added. The vial was then sealed and the mixture was reacted at 30° C. for 12 hours. The same analysis as in Example 1 was conducted, and a production of 0.8 μM methyl methacrylate was confirmed (Table 1).

Also, using a 0.1 mM methyl methacrylate solution (50 mM Tris-HCl, pH 8.5), hydrolysis reaction of a methacrylic acid ester was confirmed. The reaction was carried out at 30° C. for 3 hours. The result is shown in Table 2.

Example 3

Synthesizing Butyl Methacrylate by *Vitis vinifera*

The reaction was carried out the same as in Example 2 except that methanol was replaced with n-butanol. As a result, a production of 9.0 µm butyl methacrylate was confirmed. The hydrolysis reaction of the methacrylic acid ester was also confirmed the same as in Example 2.

Example 4

Synthesizing Hexyl Methacrylate by *Citrusxparadisi*

Two grams of loosened juice sac of a *Citrusxparadisi* fruit was measured in a vial, to which 0.5 mL of a substrate solution (50 mM Tris-HCl (pH 8.5, 40 mM n-hexanol, 10 mM methacrylyl-CoA) was added. The vial was sealed and the mixture was reacted at 30° C. for 12 hours. The same analysis as in Example 1 was performed, and a production of 0.3 µM hexyl methacrylate was confirmed.

Example 5

Synthesizing Ethyl Methacrylate by *Durio zibethinus*

One gram of a *Durio zibethinus* fruit was finely chopped and measured in a vial, to which 0.5 mL of a substrate solution (50 mM Tris-HCl (pH 8.5, 40 mM ethanol, 0.125 mM methacrylyl-CoA) was added. The vial was sealed and the mixture was reacted at 30° C. for 3 hours. The same analysis as in Example 1 was performed, and production of 6.7 µM ethyl methacrylate was confirmed.

Also, using a 0.1 mM ethyl methacrylate solution (50 mM Tris-HCl, pH 8.5), hydrolysis reaction of a methacrylic acid ester was confirmed. The reaction was carried out at 30° C. for 3 hours. The result is shown in Table 2.

Example 6

Synthesizing Butyl Methacrylate by *Durio zibethinus*

The reaction was carried out the same as in Example 5 except that ethanol was replaced with n-butanol. As a result, production of 14 µM butyl methacrylate was confirmed. The hydrolysis reaction of the methacrylic acid ester was also confirmed the same as in Example 5.

Example 7

Synthesizing Butyl Methacrylate by *Magnolia figo*

One gram and 0.5 grams respectively of chopped leaf and flower bud of *Magnolia figo* were measured in vials, to which 1 mL of a substrate solution (50 mM Tris-HCl (pH 8.5), 40 µmM n-butanol, 0.125 mM methacrylyl-CoA) was added. The vials were sealed and the mixtures were reacted at 30° C. for 12 hours. The same analysis as in Example 1 was performed, and productions of 4.4 µM and 0.4 µM butyl methacrylate were confirmed respectively.

Also, using a 0.01 mM butyl methacrylate solution (50 mM Tris-HCl, 8.5), hydrolysis reaction of a methacrylic acid ester was confirmed. The reaction was carried out at 30° C. for 12 hours. The results are shown in Table 2.

Example 8

Synthesizing Butyl Methacrylate by *Chamaemelum nobile*

In a vial, 0.5 grams of chopped leaf of *Chamaemelum nobile* was measured, to which 0.5 µmL of a substrate solution (50 mM Tris-HCl (pH 8.5), 40 mM n-butanol, 0.125 mM methacrylyl-CoA) was added. The vial was sealed and the mixture was reacted at 30° C. for 12 hours. The same analysis as in Example 1 was performed, and production of 6.7 µM butyl methacrylate was confirmed.

Also, using a 0.1 mM butyl methacrylate solution (50 mM Tris-HCl, pH 8.5), hydrolysis reaction of a methacrylic acid ester was confirmed. The reaction was carried out at 30° C. for 3 hours. The result is shown in Table 2.

Example 9

Purifying AAT Derived from *Chamaemelum nobile*

Unless otherwise specified, enzymes were purified at a temperature of 4° C. or lower. The AAT activity in each fraction was analyzed through GC using n-butanol and methacrylyl-CoA as the substrate.

(1) Preparing Crude Enzyme Liquid

In liquid nitrogen, 38 grams of *Chamaemelum nobile* leaves were made into powder. The powder was then suspended in 190 mL of extraction buffer (10% glycerol, 5 mM dithiothreitol (DTT), 5% polyvinylpyrrolidone, and 250 mM Tris-HCl (pH 7.5)), and the suspension was filtrated through a four-layer gauze. The filtrate was centrifuged at 15,000 g for 15 minutes. Accordingly, a crude enzyme liquid was obtained.

(2) Method for Determining AAT Activity

In a 2 mL capacity screw vial (Autosampler Vials, made by National Scientific), 500 µL of a reaction solution (50 mM Tris-HCl (pH 8.0), 40 mM n-butanol, 0.12 mM methacrylyl-CoA) was prepared. Then, the purified enzyme in each of steps (3)~(6) below was added, the vial was sealed, and the mixture was reacted at 30° C. for an hour.

After the reaction, 50 µL of 10 mM 2-hexanon was added as the internal standard, and solvent extraction was performed using 200 µL of octane. The mixture was centrifuged and 8 µL of the separated liquid was injected into GC, and the amount of butyl methacrylate produced in the enzymatic reaction was measured. The amount of methacrylic acid ester was measured by the calibration curve prepared using an internal standard method.

GC Analysis Conditions column: DB-WAX (inner dia. 0.25 mm×60 m, 0.5 µm, Agilent Technologies)

column temperature: 115° C.·5 min→40° C./min→200° C.·2 min carrier gas: helium detection: FID injection temperature: 230° C.

detection temperature: 250° C.

(3) Purification by DEAE-Toyopearl Column (Twice)

The crude enzyme liquid was supplied to a DEAE-Toyopearl column (20 mL), which was equilibrated with a 250 mM Tris-HCl buffer (pH 8.0) containing 10% glycerol and 2 mM DTT. The flow-through fraction was collected and subjected to dialysis against a 20 mM Tris-HCl buffer (pH 8.0) containing 10% glycerol and 2 mM DTT (hereinafter referred to as buffer B).

Furthermore, the dialyzed fraction was supplied again to a DEAE-Toyopearl column (10 mL) equilibrated with buffer B. The fraction was washed well with buffer B, and then eluted with a linear gradient of sodium chloride raised from 0 M to 0.3 M. The eluate was divided into 5.5 mL fractions. The elution patterns are shown in FIG. 1. The obtained AAT active fraction was collected and dialyzed against buffer B. In the graph, for "AAT activity" (white dots), the amount of enzyme to produce 1 µmol of ester per minute was set as 1 U. "Protein concentration" (black dots) was measured by a Bio-Rad protein assay Kit (Bio-Rad, USA) that uses bovine serum albumin as the standard.

(4) Purification by Q Sepharose Column

Figure 2:
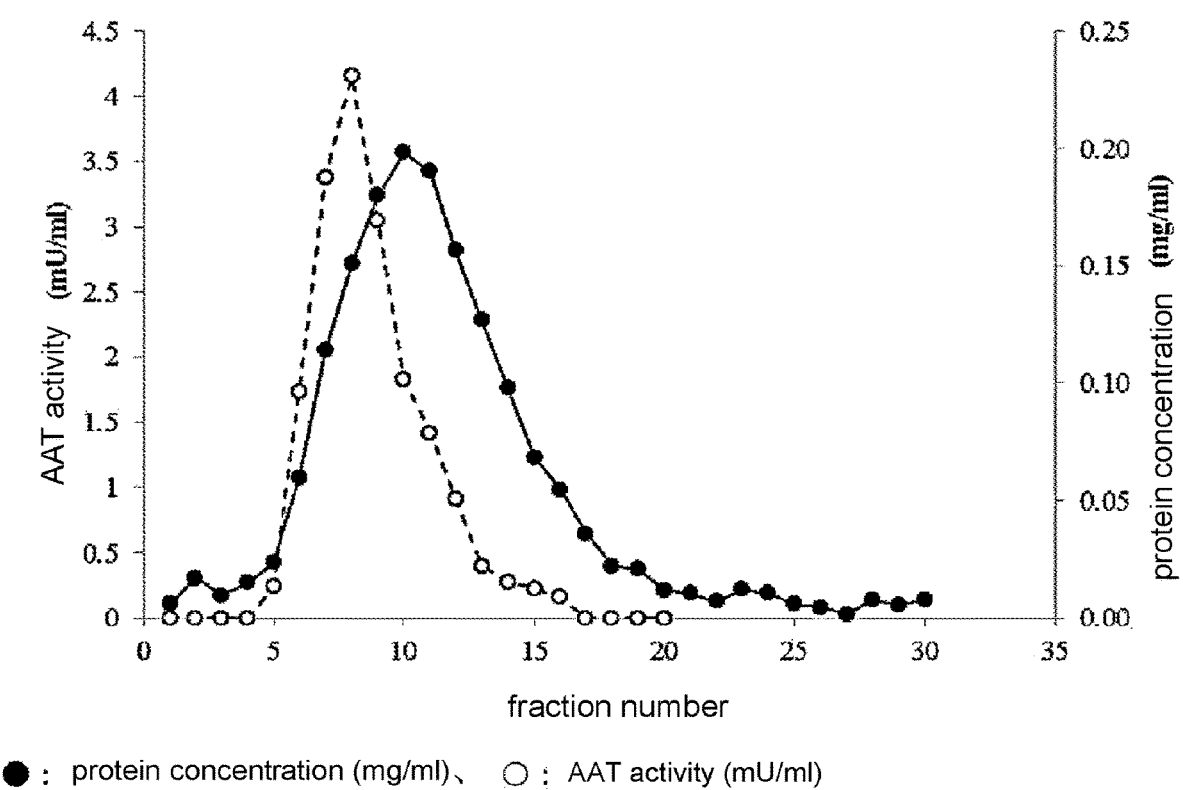
FIG. 2 is a graph showing purification conducted through a Q-Sepharose column (elution patterns)

The dialyzed AAT active fraction was supplied to a Q Sepharose column (10 mL) equilibrated with buffer B. The liquid was washed well with buffer B, and then eluted with a linear gradient of sodium chloride raised from 0 M to 0.3 M. The eluate was divided into 5.5 mL fractions. The elution patterns are shown in FIG. 2. Then, the obtained AAT active fraction was collected and dialyzed against a 20 mM Tris-HCl buffer (pH 8.0) containing 2 mM DTT (hereinafter referred to as buffer C).

(5) Purification by MonoQ 5/50 GL Column

Figure 3:
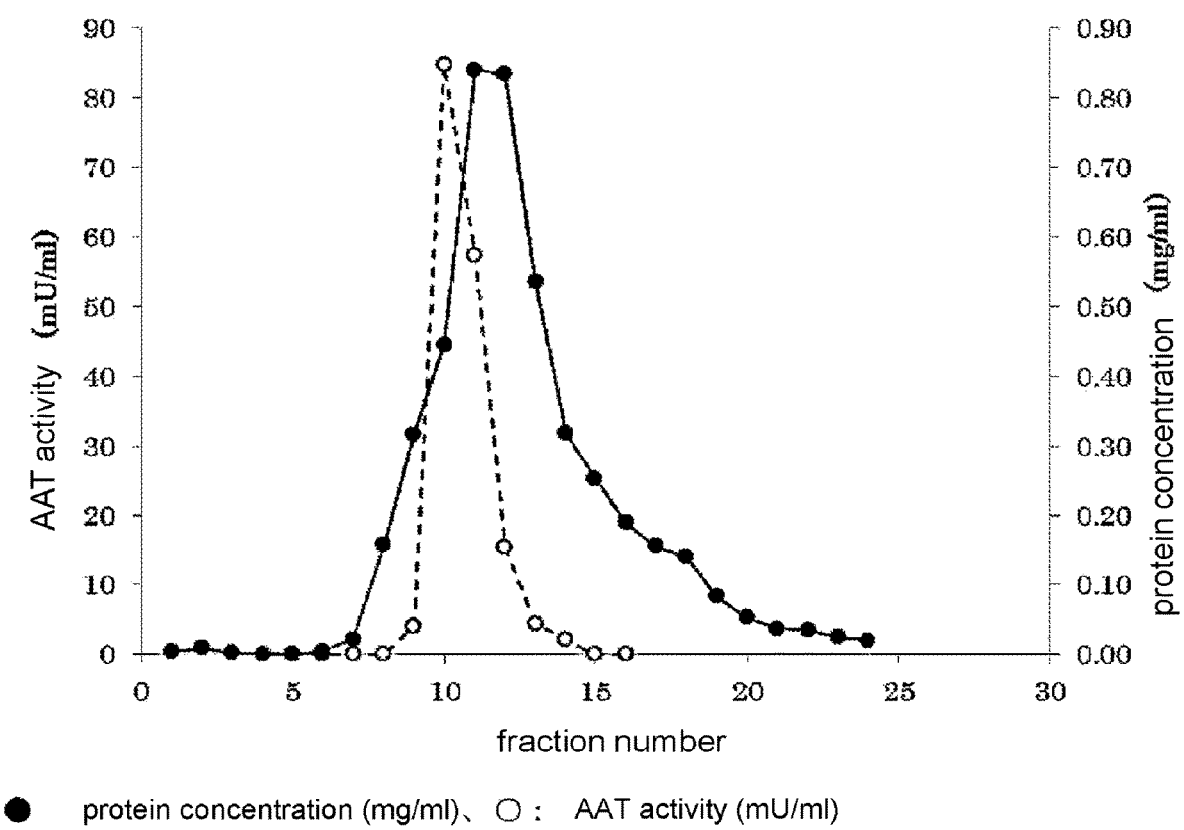
FIG. 3 is a graph showing purification through a MonoQ 5/50 GL column (elution patterns)

The dialyzed AAT active fraction obtained by the Q Sepharose column chromatography was supplied to a MonoQ 5/50 GL column (1 mL) equilibrated with buffer C, and then eluted with a linear gradient of sodium chloride raised from 0 M to 0.5 M. The elution patterns are shown in FIG. 3. The AAT active fraction was collected and concentrated using Amicon Ultra-0.5 mL centrifugal filter. Purification by the present column was conducted using an AKTA Explorer 10S (GE Healthcare) under a flow-rate condition of 0.5 mL/min. The eluate was divided into 0.5 mL fractions.

(6) Purification by Superdex 200 10/300 GL Column

Figure 4:
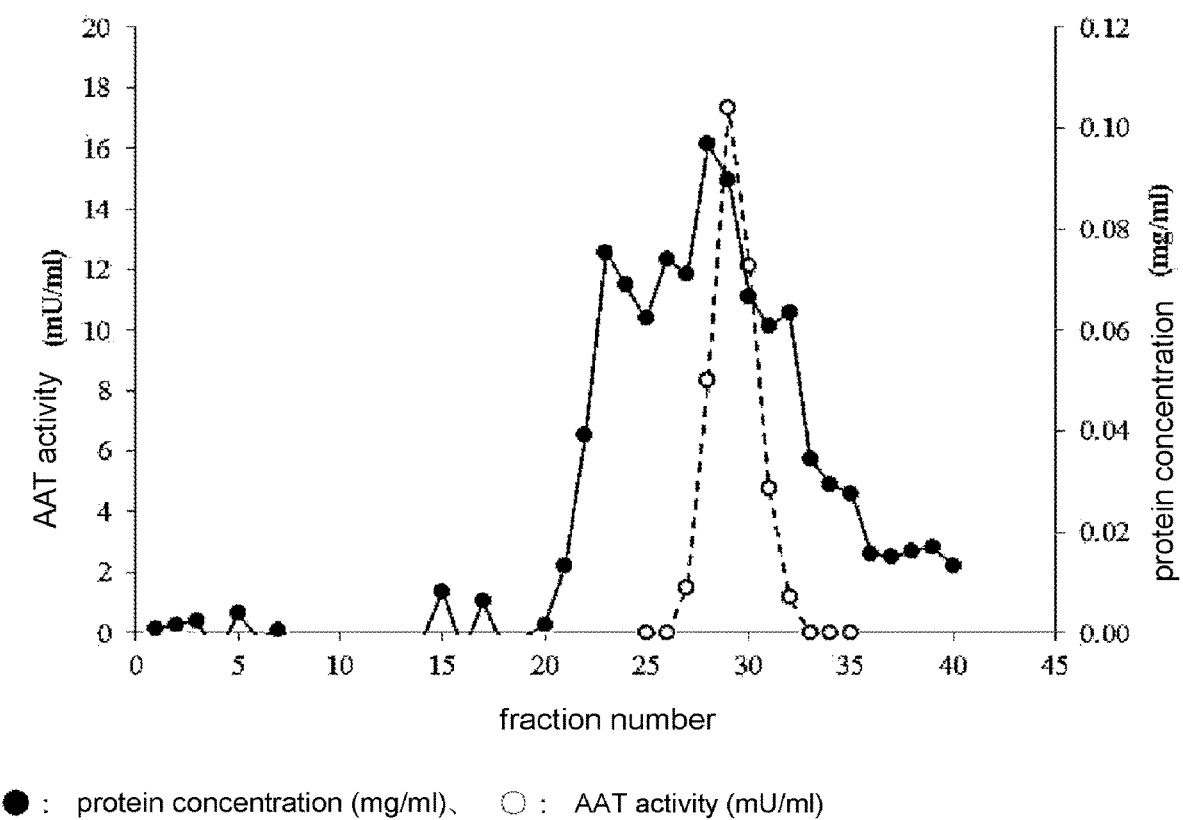
FIG. 4 is a graph showing purification through Superdex 200 10/300 GL column (elution patterns)

The concentrated AAT active fraction obtained by the MonoQ 5/50 GL column chromatography was supplied to a Superdex 200 10/300 GL column equilibrated with buffer C containing 0.3 M sodium chloride. The purification by the present column was conducted under a flow-rate condition of 0.5 mL/min using AKTA Explorer 10S and the eluate was divided into 0.5 mL fractions. The elution patterns are shown in FIG. 4. The AAT active fraction was collected and subjected to dialysis against buffer B.

(7) Summary of Each Purification Stage

Table 3 shows the collected amount and activity of the enzyme composition at each purification stage. After performing column separation five times, 201 mU/mg AAT was obtained and purified to have 209 times the initial activity.

TABLE 3

| Purification process | Total activity (mU) | Total protein amount (mg) | Specific activity (mU/mg) | Yield of activity (%) | Purity (times) |
|---|---|---|---|---|---|
| crude enzyme liquid | 210 | 219 | 0.96 | 100 | 1 |
| DEAE-Toyopearl column (1st time) | 153 | 200 | 0.76 | 72.8 | 0.8 |
| DEAE-Toyopearl column (2nd time) | 110 | 10.5 | 10.5 | 52.4 | 10.9 |
| Q-Sepharose column | 81.9 | 3.19 | 25.7 | 38.9 | 26.7 |
| MonoQ 5/50 GL column | 42.3 | 0.5 | 84.8 | 20.1 | 88.3 |
| Superdex 200 10/300 GL column | 9.6 | 0.05 | 201 | 4.56 | 209 |

Example 10

Substrate Specificity of AAT Derived from *Chamaemelum nobile*

The substrate specificity of AAT was evaluated by the purified fraction obtained by MonoQ 5/50 GL column chromatography in Example 9.

In a 2-mL capacity screw vial, a reaction solution (50 mM Tris-HCl (pH 8.5), 40 mM alcohol, 0.12 mM acyl-CoA) was prepared, into which the purified fraction was added to be 500 μL. The vial was sealed and the mixture was reacted at 30° C. for one hour.

After the reaction was completed, 50 μL of 10 mM 2-hexanon was added as the internal sstandard, and solvent extraction was conducted using 200 μL octane or hexane. Centrifugation was conducted and 8 μL of the separated liquid was injected into GC to measure the ester produced through the enzymatic reaction. The amount of ester was calculated by the calibration curve using an internal standard method. The GC measuring conditions were set the same as in Example 9 except that the column temperature was adjusted appropriately for each of the target esters (see Table 4). To determine the quantity of n-butyl propionate, since the present column is unable to separate its peak from the peak of n-butanol, the absolute calibration curve method was employed under the GC-MS analysis conditions the same as in Example 1 (however, temperature conditions were changed to 80° C.→1 min→10° C./min→200° C.·5 min).

TABLE 4

| Ester | Extraction solvent | Column temperature condition | Retention time (min) |
|---|---|---|---|
| methyl acetate | hexane | 35° C., 9 min-40° C./min-200° C., 2 min | 4.1 |
| ethyl acetate | hexane | 45° C., 9 min-40° C./min-200° C., 2 min | 4.6 |
| n-butyl acetate | octane | 90° C., 4 min-40° C./min-200° C., 2 min | 4.2 |
| n-hexyl acetate | octane | 90° C., 4 min-40° C./min-200° C., 2 min | 6.3 |
| methyl propionate | hexane | 50° C., 8 min-40° C./min-200° C., 2 min | 4.6 |
| methyl isobutyrate | octane | 60° C., 7 min-40° C./min-200° C., 2 min | 4.1 |
| ethyl isobutyrate | hexane | 70° C., 7 min-40° C./min-200° C., 2 min | 4.0 |
| n-butyl isobutyrate | hexane | 90° C., 6 min-40° C./min-200° C., 2 min | 5.2 |
| methyl methacrylate | octane | 90° C., 4 min-40° C./min-200° C., 2 min | 3.5 |
| ethyl methacrylate | octane | 100° C., 4 min-40° C./min-200° C., 2 min | 3.3 |
| n-butyl methacrylate | octane | 115° C., 5 min-40° C./min-200° C., 2 min | 4.7 |
| n-hexyl methacrylate | octane | 120° C., 7 min-40° C./min-200° C., 2 min | 6.6 |
| methyl n-butyrate | hexane | 70° C., 7 min-40° C./min-200° C., 2 min | 4.5 |
| n-butyl n-butyrate | octane | 105° C., 5 min-40° C./min-200° C., 2 min | 4.7 |
| methyl hexanoate | octane | 115° C., 5 min-40° C./min-200° C., 2 min | 4.4 |
| ethyl hexanoate | octane | 115° C., 5 min-40° C./min-200° C., 2 min | 4.9 |
| n-butyl hexanoate | octane | 120° C., 7 min-40° C./min-200° C., 2 min | 7.8 |

The results are shown in Table 5. Relative activity values are shown based on the specific activity of butyl methacrylate set as 100%.

TABLE 5

| Substrate | | methanol | ethanol | n-butanol | n-hexanol |
|---|---|---|---|---|---|
| acetyl-CoA | CH₃-C(=O)-S-CoA | N.D. | N.D. | 37 | 84 |
| propionyl-CoA | CH₃CH₂-C(=O)-S-CoA | 4 | N.T. | 136 | N.T. |
| isobutyryl-CoA | (CH₃)₂CH-C(=O)-S-CoA | N.D. | 5 | 114 | N.T. |
| methacrylyl-CoA | CH₂=C(CH₃)-C(=O)-S-CoA | 1 | 4 | 100 | 182 |
| butyryl-CoA | CH₃CH₂CH₂-C(=O)-S-CoA | N.D. | N.T. | 40 | N.T. |
| hexanoyl-CoA | CH₃(CH₂)₄-C(=O)-S-CoA | N.D. | 11 | 21 | N.T. |

* N.D = not detected, N.T. = not conducted

Example 11

Optimum pH of AAT Derived from *Chamaemelum nobile*

The optimum pH was evaluated on the purified fraction obtained by MonoQ 5/50 GL column chromatography in Example 9.

Using an acetate buffer, PIPES buffer (peperazine-1,4-bis (2-ethanesulfonic acid)), Tris (tris(hydroxymethyl)aminomethane)-HCl buffer, or glycine-sodium hydroxide buffer, a reaction composition containing 40 mM n-butanol and 0.12 mM methacrylyl-CoA were each prepared. The concentration of each buffer was set at 50 mM. Then, the purified fraction was added to each reaction composition to be 500 μL. The vial was sealed, and reaction was carried out at 30° C. for an hour.

Figure 5:
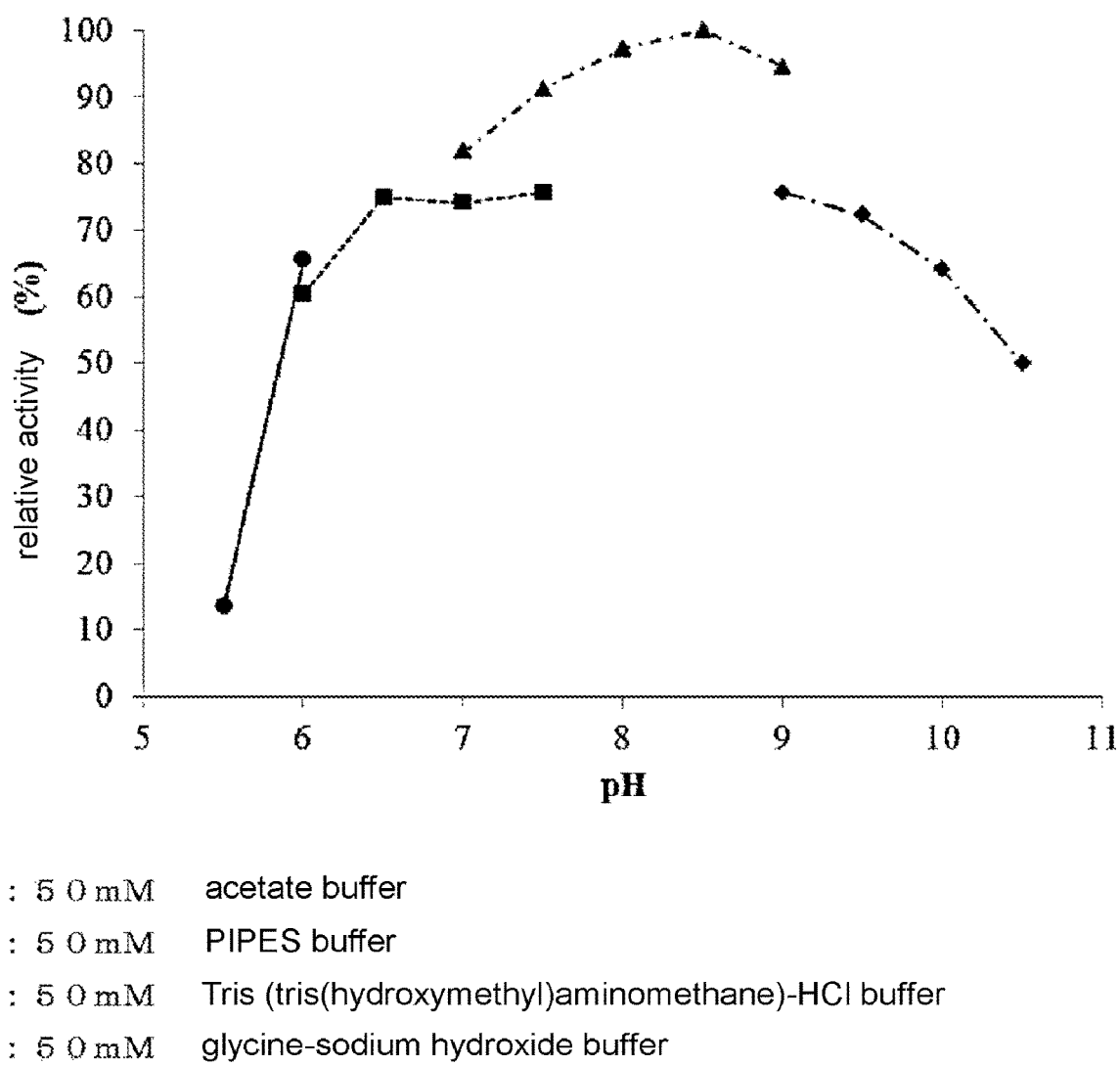
FIG. 5 is a graph showing the measurement results of optimum pH of AAT derived from *Chamaemelum nobile*.

After the reaction was completed, GC analysis the same as in Example 9 was conducted to measure butyl methacrylate produced in the enzymatic reaction. The results are shown in FIG. 5. In the graph, circles denote the result in the acetate buffer, squares denote the result in the PIPES buffer, triangles denote the result in the Tris (tris(hydroxymethyl) aminomethane)-HCl buffer, and diamonds denote the result in the glycine-sodium hydroxide buffer. The optimum pH was 8~9.

Example 12

Km of AAT Derived from *Chamaemelum nobile*

The Km values for methacrylyl-CoA and acetyl-CoA were measured using the purified fraction obtained by MonoQ 5/50 GL column chromatography in Example 9. A 500 μL reaction solution was prepared by adding the purified fraction, 40 mM n-hexanol and methacrylyl-CoA or acetyl-CoA at each concentration to a 50 mM Tris-HCl buffer (pH 8.5). The vial was sealed, and reaction was carried out at 30° C. for 2 hours.

Figure 6:
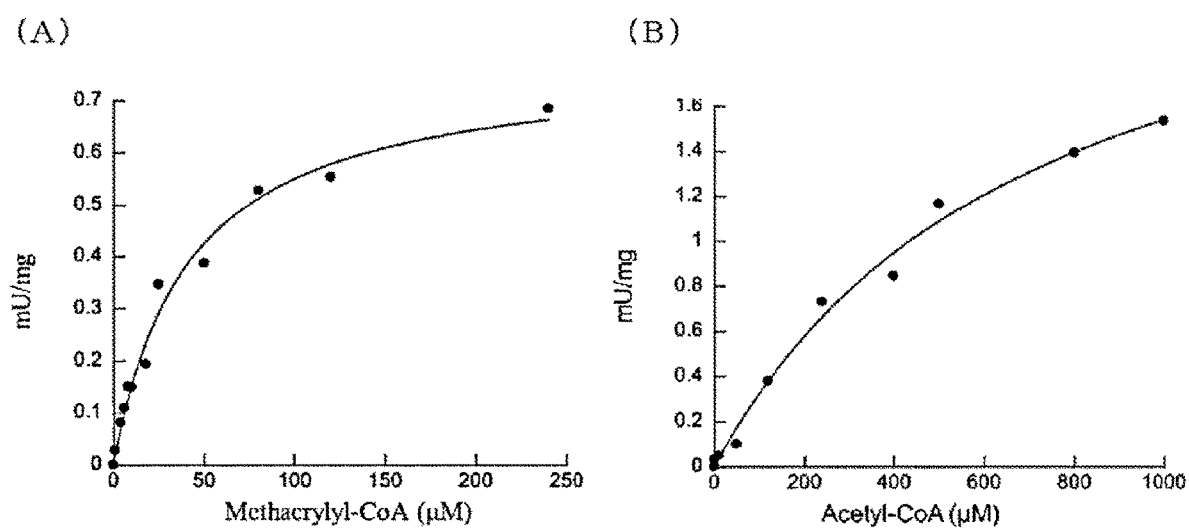
FIG. 6 is a graph showing the relationships between the substrate concentration and reaction rates of AAT derived from *Chamaemelum nobile*: graph (A) shows the results using methacrylyl-CoA, and graph (B) shows the results using acetyl-CoA.

After the reaction was completed, the same GC analysis as in Example 10 was conducted to measure the ester produced in the enzymatic reaction. The results are shown in FIG. 6. The rate constant (Km) was applied to a Michaelis-Menten expression to calculate the values using a Kaleidagraph software made by HULINKS. Accordingly, the Km value for methacrylyl-CoA was determined to be 0.041 mM, and the Km value for acetyl-CoA was 0.711 mM.

What is claimed is:

1. A method for producing a methacrylic acid ester, comprising:
synthesizing a methacrylic acid ester by reacting alcohol or phenol with methacrylyl-CoA in the presence of an alcohol acyltransferase derived from a plant selected from the group consisting of plants that belong to *Durio* and *Chamaemelum*.

2. The method for producing a methacrylic acid ester according to claim 1, in which the plant is selected from the group consisting of *Durio zibethinus* and *Chamaemelum nobile*.

* * * * *